United States Patent [19]

Gilroy et al.

[11] Patent Number: 5,128,130

[45] Date of Patent: Jul. 7, 1992

[54] HYBRID BACILLUS THURINGIENSIS GENE, PLASMID AND TRANSFORMED PSEUDOMONAS FLUORESCENS

[75] Inventors: Thomas E. Gilroy, San Diego; Edward R. Wilcox, Escondido, both of Calif.

[73] Assignee: Mycogen Corporation, San Diego, Calif.

[21] Appl. No.: 568,650

[22] Filed: Aug. 14, 1990

Related U.S. Application Data

[63] Continuation of Ser. No. 146,997, Jan. 22, 1988, abandoned.

[51] Int. Cl.$^5$ .............. A01N 63/00; C12N 1/21; C12N 15/32
[52] U.S. Cl. ................ 424/93 A; 536/27; 530/350; 435/69.1; 435/71.2; 435/91; 435/170; 435/172.1; 435/172.3; 435/252.3; 435/320.1; 435/832; 435/848; 435/874; 935/6; 935/9; 935/10; 935/22; 935/27; 935/59; 935/60; 935/61
[58] Field of Search ............ 576/27; 530/350; 435/691, 71.2, 91, 170, 172.1, 172.3, 252.3, 320.1; 935/6, 9, 10, 22, 27, 59, 60, 61, 63, 66, 72; 424/93

[56] References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 435/317 |
| 4,771,131 | 9/1988 | Hernstadt et al. | 536/27 |

OTHER PUBLICATIONS

Schnepf, H. E., and Whitely, H. R. (1981) "Cloning and Expression of the *Bacillus thuringiensis* Crystal Protein Gene in *E. coli*", Proc. Natl. Acad. Sci. U.S.A. 78:2893-2897.

Adarq et al., 1985, *Gene*, 36:389-300.

Primary Examiner—Richard C. Peet
Attorney, Agent, or Firm—Saliwanchik & Saliwanchik

[57] ABSTRACT

A novel hyrid *B.t.* toxin gene toxic to lepidopteran insects has been cloned. The DNA encoding the *B.t.* toxin can be used to transform various prokaryotic and eukaryotic microbes to express the *B.t.* toxin. These recombinant microbes can be used to control lepidopteran insects in various environments.

27 Claims, 9 Drawing Sheets

FIGURE 1-1

```
              5                   10                  15                  20
Met Asp Asn Pro Asn Ile Asn Glu Cys Ile Pro Tyr Asn Cys Leu Ser Asn Pro Glu
ATG GAT AAC CCG AAC ATC AAT GAA TGC ATT CCT TAT AAT TGT TTA AGT AAC CCT GAA 25                  30                  35                  40
Val Glu Val Leu Gly Gly Glu Arg Ile Glu Thr Gly Tyr Thr Pro Ile Asp Ile Ser Leu
GTA GAA GTA TTA GGT GGA GAA AGA ATA GAA ACT GGT TAC ACC CCA ATC GAT ATT TCC TTG 45                  50                  55                  60
Ser Leu Thr Gln Phe Leu Leu Ser Glu Phe Val Pro Gly Ala Gly Phe Val Leu Gly Leu
TCG CTA ACG CAA TTT CTT TCT AGT GAA TTT GTT CCC GGT GCT GGA TTT GTG TTA GGA CTA 65                  70                  75                  80
Val Asp Ile Ile Trp Gly Ile Phe Gly Pro Ser Gln Trp Asp Ala Phe Leu Val Gln Ile
GTT GAT ATA ATA TGG GGA ATT TTT GGT CCC TCT CAA TGG GAC GCA TTT CTT GTA CAA ATT 85                  90                  95                  100
Glu Gln Leu Ile Asn Gln Arg Ile Glu Glu Phe Ala Arg Asn Gln Ala Ile Ser Arg Leu
GAA CAG CTT ATT AAC CAA AGA ATA GAA GAA TTC GCT AGG AAC CAA GCC ATT TCT AGA TTA 105                 110                 115                 120
Glu Gly Leu Ser Asn Leu Tyr Gln Ile Tyr Ala Glu Ser Phe Arg Glu Trp Glu Ala Asp
GAA GGA CTA AGC AAT CTT TAT CAA ATT TAC GCA GAA TCT TTT AGA GAG TGG GAA GCA GAT 125                 130                 135                 140
Pro Thr Asn Pro Ala Leu Arg Glu Glu Met Arg Ile Gln Phe Asn Asp Met Asn Ser Ala
CCT ACT AAT CCA GCA TTA AGA GAA GAG ATG CGT ATT CAA TTC AAT GAC ATG AAC AGT GCC
```

FIGURE 1-2

| | | | | 145 | | | 150 | | | 155 | | | 160 |
|---|---|---|---|---|---|---|---|---|---|---|---|---|---|
| Leu | Thr | Thr | Ala | Ile | Pro | Leu | Phe | Ala | Val | Gln | Asn | Tyr | Gln | Val | Pro | Leu | Leu | Ser | Val |
| CTT | ACA | ACC | GCT | ATT | CCT | CTT | TTT | GCA | GTT | CAA | AAT | TAT | CAA | GTT | CCT | CTT | TTA | TCA | GTA |

| | | | | 165 | | | 170 | | | 175 | | | 180 |
|---|---|---|---|---|---|---|---|---|---|---|---|---|---|
| Tyr | Val | Gln | Ala | Ala | Asn | Leu | His | Leu | Ser | Val | Leu | Arg | Asp | Val | Ser | Val | Phe | Gly | Gln |
| TAT | GTT | CAA | GCT | GCA | AAT | TTA | CAT | TTA | TCA | GTT | TTG | AGA | GAT | GTT | TCA | GTG | TTT | GGA | CAA |

| | | | | 185 | | | 190 | | | 195 | | | 200 |
|---|---|---|---|---|---|---|---|---|---|---|---|---|---|
| Arg | Trp | Gly | Phe | Asp | Ala | Ala | Thr | Ile | Asn | Ser | Arg | Tyr | Asn | Asp | Leu | Thr | Arg | Leu | Ile |
| AGG | TGG | GGA | TTT | GAT | GCC | GCG | ACT | ATC | AAT | AGT | CGT | TAT | AAT | GAT | TTA | ACT | AGG | CTT | ATT |

| | | | | 205 | | | 210 | | | 215 | | | 220 |
|---|---|---|---|---|---|---|---|---|---|---|---|---|---|
| Gly | Asn | Tyr | Thr | Asp | Tyr | Ala | Val | Arg | Trp | Tyr | Asn | Thr | Gly | Leu | Glu | Arg | Val | Trp | Gly |
| GGC | AAC | TAT | ACA | GAT | TAT | GCT | GTA | CGT | TGG | TAC | AAT | ACG | GGA | TTA | GAA | CGT | GTA | TGG | GGA |

| | | | | 225 | | | 230 | | | 235 | | | 240 |
|---|---|---|---|---|---|---|---|---|---|---|---|---|---|
| Pro | Asp | Ser | Arg | Asp | Trp | Val | Arg | Tyr | Asn | Gln | Phe | Arg | Arg | Glu | Leu | Thr | Leu | Thr | Val |
| CCG | GAT | TCT | AGA | GAT | TGG | GTA | AGG | TAT | AAT | CAA | TTT | AGA | AGA | GAA | TTA | ACA | CTA | ACT | GTA |

| | | | | 245 | | | 250 | | | 255 | | | 260 |
|---|---|---|---|---|---|---|---|---|---|---|---|---|---|
| Leu | Asp | Ile | Val | Ala | Leu | Phe | Pro | Asn | Tyr | Asp | Ser | Arg | Arg | Tyr | Pro | Ile | Arg | Thr | Val |
| TTA | GAT | ATC | GTT | GCT | CTG | TTC | CCG | AAT | TAT | GAT | AGT | AGA | AGA | TAT | CCA | ATT | CGA | ACT | GTT |

| | | | | 265 | | | 270 | | | 275 | | | 280 |
|---|---|---|---|---|---|---|---|---|---|---|---|---|---|
| Ser | Gln | Leu | Thr | Arg | Glu | Ile | Tyr | Thr | Asn | Pro | Val | Leu | Glu | Asn | Phe | Asp | Gly | Ser | Phe |
| TCC | CAA | TTA | ACA | AGA | GAA | ATT | TAT | ACA | AAC | CCA | GTA | TTA | GAA | AAT | TTT | GAT | GGT | AGT | TTT |

FIGURE 1-3

| | | 295 | | | | | | | 300 |
|---|---|---|---|---|---|---|---|---|---|
| Arg | Gly | Ser | Ala | Gly | Ile | Glu | Arg | Ser | Pro | His | Leu | Met | Asp | Ile | Leu |
| CGA | GGC | TCG | GCT | GGC | ATA | GAA | AGA | AGT | CCA | CAT | TTG | ATG | GAT | ATA | CTT |

| | | 305 | | | | | | | 310 | | | | | | 320 |
| Asn | Ser | Ile | Thr | Tyr | Thr | Asp | Ala | His | Arg | Gly | Tyr | Tyr | Trp | Ser | Gly | His | Gln |
| AAC | AGT | ATA | ACC | TAT | ACG | GAT | GCT | CAT | AGG | GGT | TAT | TAT | TGG | TCA | GGG | CAT | CAA |

| | | 325 | | | | | | | 330 | | | | | | 340 |
| Ile | Met | Ala | Ser | Pro | Val | Gly | Phe | Ser | Gly | Pro | Glu | Phe | Thr | Pro | Leu | Tyr | Gly | Thr |
| ATA | ATG | GCT | TCT | CCT | GTA | GGG | TTT | TCG | GGG | CCA | GAA | TTC | ACT | CCG | CTA | TAT | GGA | ACT |

| | | 345 | | | | | | | 350 | | | | | | 360 |
| Met | Gly | Asn | Ala | Ala | Pro | Gln | Gln | Arg | Val | Ala | Gln | Leu | Gly | Val | Tyr | Arg |
| ATG | GGA | AAT | GCA | GCT | CCA | CAA | CAA | CGT | GTT | GCT | CAA | CTA | GGC | GTG | TAT | AGA |

| | | 355 | | | | | | | 370 | | | | | | 380 |
| Thr | Leu | Ser | Ser | Thr | Leu | Tyr | Arg | Arg | Phe | Asn | Ile | Gly | Ile | Asn | Asn | Gln | Gln | Leu |
| ACA | TTA | TCG | TCC | ACT | TTA | TAT | AGA | AGA | TTT | AAT | ATA | GGG | ATA | AAT | AAT | CAA | CAA | CTA |

| | | 385 | | | | | | | 390 | | | | | | 400 |
| Ser | Val | Leu | Asp | Gly | Thr | Glu | Phe | Ala | Tyr | Gly | Thr | Ser | Ser | Asn | Leu | Pro | Ser | Ala | Val |
| TCT | GTT | CTT | GAC | GGG | ACA | GAA | TTT | GCT | TAT | GGA | ACC | TCC | TCA | AAT | TTG | CCA | TCC | GCT | GTA |

| | | 405 | | | | | | | 410 | | | | | | 420 |
| Tyr | Arg | Lys | Ser | Gly | Thr | Val | Asp | Ser | Leu | Asp | Glu | Ile | Pro | Gln | Asn | Asn | Val |
| TAC | AGA | AAA | AGC | GGA | ACG | GTA | GAT | TCG | CTG | GAT | GAA | ATA | CCG | CAG | AAT | AAC | GTG |

FIGURE 1-4

```
                            425                430                435                440
Pro Pro Arg Gln Gly Phe Ser His Arg Leu Ser His Val Ser Met Phe Arg Ser Gly Phe
CCA CCT AGA CAA GGA TTT AGT CAT CGA TTA AGC CAT GTT TCA ATG TTT CGT TCA GGC TTT 445                450                455                460
Ser Asn Ser Ser Val Ser Ile Ile Arg Ile Ala Pro Met Phe Ser Trp Ile His Arg Ser Ala
AGT AAT AGT AGT GTA AGT ATA ATA AGA GCT CCT ATG TTC TCT TGG ATA CAT CGT AGT GCT 465                470                475                480
Glu Phe Asn Asn Ile Ile Ala Ser Asp Ser Ile Thr Gln Ile Pro Ala Val Lys Gly Asn
GAA TTT AAT AAT ATA ATA GCA TCG GAT AGT ATT ACT CAA ATC CCT GCA GTG AAG GGA AAC 485                490                495                500
Phe Phe Asn Gly Ser Val Ile Ser Gly Pro Gly Phe Thr Gly Gly Asp Leu Val Arg
TTT CTT TTT AAT GGT TCT GTA ATT TCA GGA CCA GGA TTT ACT GGT GGC GAC TTA GTT AGA 505                510                515                520
Leu Asn Ser Ser Gly Asn Asn Ile Gln Asn Arg Gly Tyr Ile Glu Val Pro Ile His Phe
TTA AAT AGT AGT GGA AAT AAT ATT CAG AAT AGA GGG TAT ATT GAA GTT CCA ATT CAC TTC 525                530                535                540
Pro Ser Thr Ser Arg Tyr Arg Val Arg Ser Ser Val Arg Tyr Ala Ser Val Thr Pro Ile His
CCA TCG ACA TCT AGA TAT CGA GTT CGT TCC TCT GTA TAT GCT TCT GTA ACC CCG ATT CAC 545                550                555                560
Leu Asn Val Asn Trp Gly Asn Ser Ile Phe Ser Asn Thr Val Pro Ala Thr Ala Thr Thr
CTC AAC GTT AAT TGG GGT AAT TCC ATT TTT TCC AAT ACA GTA CCA GCT ACA GCT ACG 565                570                575                580
Ser Leu Asp Asn Leu Gln Ser Ser Asp Phe Gly Tyr Phe Glu Ser Ala Asn Ala Phe Thr
TCA TTA GAT AAT CTA CAA TCA AGT GAT TTT GGT TAT TTT GAA AGT GCC AAT GCT TTT ACA
```

FIGURE 1-5

```
                585             590             595             600
Ser Ser Leu Gly Asn Ile Val Gly Val Arg Asn Phe Ser Gly Ala Gly Val Ile Ile
TCT TCA TTA GGT AAT ATA GTA GGT GTT AGA AAT TTT AGT GGG GCA GGA GTG ATA 605             610             615             620
Asp Arg Phe Glu Phe Ile Pro Val Thr Ala Thr Leu Glu Ala Glu Tyr Asn Leu Arg
GAC AGA TTT GAA TTT ATT CCA GTT ACT GCA ACA CTC GAG GCT GAA TAT AAT CTG AGA 625             630             635             640
Ala Gln Lys Ala Val Asn Ala Leu Phe Thr Ser Thr Asn Gln Leu Gly Leu Lys Thr Asn
GCG CAG AAG GCG GTG AAT GCG CTG TTT ACG TCT ACA AAC CAA CTA GGG CTA AAA ACA AAT 645             650             655             660
Val Thr Asp Tyr His Ile Asp Gln Val Ser Asn Leu Val Thr Tyr Leu Ser Asp Glu Phe
GTA ACG GAT TAT CAT ATT CAA TCC AAT TTA GTT ACG TAT TTA TCG GAT GAA TTT 665             670             675             680
Cys Leu Asp Glu Lys Arg Glu Leu Ser Glu Lys Val Lys His Ala Lys Arg Leu Ser Asp
TGT CTG GAT GAA AAG CGA GAA TTG TCC GAG AAA GTC AAA CAT GCG AAG CGA CTC AGT GAT 685             690             695             700
Glu Arg Asn Leu Leu Gln Asp Ser Asn Phe Lys Asp Ile Asn Arg Gln Pro Glu Arg Gly
GAA CGC AAT TTA CTC CAA GAT TCA AAT TTC AAA GAC ATT AAT AGG CAA CCA GAA CGT GGG 705             710             715             720
Trp Gly Gly Ser Thr Gly Ile Thr Ile Gln Gly Gly Asp Asp Val Phe Lys Glu Asn Tyr
TGG GGC GGA AGT ACA GGG ATT ACC ATC CAA GGA GAT GAC GTA TTT AAA GAA AAT TAC
```

FIGURE 1-6

```
        725              730              735              740
Val Thr Leu Ser Gly Thr Phe Asp Glu Cys Tyr Pro Thr Tyr Leu Gln Lys Ile Asp
GTC ACA CTA TCA GGT ACC TTT GAT GAG TGC TAT CCA ACA TAT TTG CAA AAA ATC GAT 750              755              760
Glu Ser Lys Leu Ala Phe Thr Arg Tyr Gln Leu Arg Gly Tyr Ile Glu Asp Ser Gln
GAA TCA AAA TTA GCC TTT ACC CGT TAT CAA TTA AGA GGG TAT ATC GAA GAT AGT CAA 765              770              775              780
Asp Leu Glu Ile Tyr Leu Ile Arg Tyr Asn Ala Lys His Glu Thr Val Asn Val Pro Gly
GAC TTA GAA ATC TAT TTA ATT CGC TAC AAT GCA AAA CAT GAA ACA GTA AAT GTG CCA GGT 790              795              800
Thr Gly Ser Leu Trp Pro Leu Ser Ala Gln Ser Pro Ile Gly Lys Cys Gly Glu Pro Asn
ACG GGT TCC TTA TGG CCG CTT TCA GCC CAA AGT CCA ATC GGA AAG TGT GGA GAG CCG AAT 805              810              815              820
Arg Cys Ala Pro His Leu Glu Trp Asn Pro Asp Leu Asp Cys Ser Cys Arg Asp Gly Glu
CGA TGC GCC CCA CAC CTT GAA TGG AAT CCT GAC TTA GAT TGT TCG TGT AGG GAT GGA GAA 830              835              840
Lys Cys Ala His His Ser His His Phe Ser Leu Asp Ile Asp Val Gly Cys Thr Asp Leu
AAG TGT GCC CAT CAT TCG CAT CAT TTC TCC TTA GAC ATT GAT GTA GGA TGT ACA GAC TTA 845              850              855              860
Asn Glu Asp Leu Gly Val Trp Val Ile Phe Lys Ile Lys Thr Gln Asp Gly His Ala Arg
AAT GAG GAC CTA GGT GTA TGG GTG ATC TTT AAG ATT AAG ACG CAA GAT GGG CAC GCA AGA 870              875              880
Leu Gly Asn Leu Glu Phe Leu Glu Glu Lys Pro Leu Val Gly Glu Ala Leu Ala Arg Val
CTA GGG AAT CTA GAG TTT CTC GAA GAG AAA CCA TTA GTA GGA GAA GCG CTA GCT CGT GTG
```

FIGURE 1-7

```
                    885                          890                            895                          900
Lys Arg Ala Glu Lys Lys Trp Arg Asp Lys Arg Glu Lys Leu Glu Trp Glu Thr Asn Ile
AAA AGA GCG GAG AAA AAA TGG AGA GAC AAA CGT GAA AAA TTA GAA TGG GAA ACA AAT ATT 905                          910                            915                          720
Val Tyr Lys Glu Ala Lys Glu Ser Val Asp Ala Leu Phe Val Asn Ser Gln Tyr Asp Gln
GTT TAT AAA GAG GCA AAA GAA TCT GTA GAT GCT TTA TTT GTA AAC TCT CAA TAT GAT CAA 925                          930                            935                          940
Leu Gln Ala Asp Thr Asn Ile Ala Met Ile His Ala Ala Asp Lys Arg Val His Ser Ile
TTA CAA GCG GAT ACG AAT ATT GCC ATG ATT CAT GCG GCA GAT AAA CGT GTT CAT AGC ATT 945                          950                            955                          760
Arg Glu Ala Tyr Leu Pro Glu Leu Ser Val Ile Pro Ala Val Asn Ala Ala Ile Phe Glu
CGA GAA GCT TAT CTG CCT GAG CTG TCT GTG ATT CCG GCT GTC AAT GCT GCT ATT TTT GAA 965                          970                            975                          980
Glu Leu Glu Gly Arg Ile Phe Thr Ala Phe Ser Leu Tyr Asp Arg Asn Val Ile Lys
GAA TTA GAA GGG CGT ATT TTC ACT GCA TTC TCC CTA TAT GAT GCG AGA AAT GTC ATT AAA 985                          990                            995                         1000
Asn Gly Asp Phe Asn Asn Gly Leu Ser Cys Trp Asn Val Lys Gly His Val Asp Val Glu
AAT GGT GAT TTT AAT AAT GGC TTA TCC TGC TGG AAC GTG AAA GGG CAT GTA GAT GTA GAA 1005                         1010                           1015                         1020
Glu Gln Asn Asn His Arg Ser Val Leu Val Val Pro Glu Trp Glu Ala Glu Val Ser Gln
GAA CAA AAC AAC CAC CGT TCG GTC CTT GTT CCG GAA TGG GAA GCA GAA GTG TCA CAA
```

FIGURE 1-8

```
                        1025                1030                1035           1040
Glu Val Arg Val Cys Pro Gly Arg Gly Tyr Ile Leu Arg Val Thr Ala Tyr Lys Glu Gly
GAA GTT CGT GTC TGT CCG GGT CGT GGC TAT ATC CTT CGT GTC ACA GCA TAC AAG GAA GGA 1045                1050                1055                1060
Tyr Gly Glu Gly Cys Val Thr Val Thr Ile His Glu Ile Glu Asn Asn Thr Asp Glu Leu Lys Phe
TAT GGA GAA GGT TGC GTA ACC ATT CAT GAG ATC GAG AAC AAT ACA GAC GAA CTG AAG TTT 1065                1070                1075                1080
Ser Asn Cys Val Glu Glu Glu Val Tyr Pro Asn Asn Thr Val Thr Cys Asn Asp Tyr Thr
AGC AAC TGT GTA GAA GAG GAA GTA TAT CCA AAC AAC ACG GTA ACG TGT AAT GAT TAT ACT 1085                1090                1095                1100
Ala Thr Gln Glu Glu Tyr Glu Ala Thr Tyr Thr Ser Arg Asn Arg Gly Tyr Asp Gly Ala
GCG ACT CAA GAA GAA TAT GAG GCT ACG TAC ACT TCT CGT AAT CGA GGA TAT GAC GGA GCC 1105                1110                1115                1120
Tyr Glu Ser Asn Ser Ser Val Pro Ala Asp Tyr Ala Ser Ala Tyr Glu Glu Lys Ala Tyr
TAT GAA AGC AAT TCT TCT GTA CCA GCT GAT TAT GCA TCA GCC TAT GAA GAA AAA GCA TAT 1125                1130                1135                1140
Thr Asp Gly Arg Arg Asp Asn Pro Cys Glu Ser Asn Arg Gly Tyr Gly Asp Tyr Thr Pro
ACA GAT GGA CGA AGA GAC AAT CCT TGT GAA TCT AAC AGA GGA TAT GGG GAT TAC ACA CCA 1145                1150                1155                1160
Leu Pro Ala Gly Tyr Val Thr Lys Glu Leu Glu Tyr Phe Pro Glu Thr Asp Lys Val Trp
CTA CCA GCT GGC TAT GTG ACA AAA GAA TTA GAG TAC TTC CCA GAA ACC GAT AAG GTA TGG 1165                1170                1175                1180
Ile Glu Gly Ile Glu Thr Gly Thr Phe Ile Val Asp Ser Val Glu Leu Leu Leu Met
ATT GAG ATC GGA GAA ACG GGA ACA TTC ATC GTG GAC AGC GTG GAA TTA CTT ATG
```

FIGURE 1-9

```
                                              1185                    1170                    1175                                 1200
Glu Glu ***
GAG GAA TAA TAT ATG CTT TAA AAT GTA AGG TGT GCA AAT AAA GAA TGA TTA CTG ACT TGT
                      1205                    1210                    1215                    1220
ATT GAC AGA TAA ATA AGG AAA TTT TTA TAT GAA TAA AAA ACG GGC ATC ACT CTT AAA AGA
                      1225                    1230                    1235
ATG ATG TCC GTT TTT TGT ATG ATT TAA CGA GTG ATA TTT AAA TGT TTT TTT GCG AAG G
```

HYBRID BACILLUS THURINGIENSIS GENE, PLASMID AND TRANSFORMED PSEUDOMONAS FLUORESCENS

This application is a continuation of application Ser. No. 07/146,997 filed Jan. 22, 1988, now abandoned.

BACKGROUND OF THE INVENTION

The most widely used microbial pesticides are derived from the bacterium *Bacillus thuringiensis*. This bacterial agent is used to control a wide range of leaf-eating caterpillars, Japanese beetles and mosquitos. *Bacillus thuringiensis* produces a proteinaceous parasapore or crystal which is toxic upon ingestion by a susceptible insect host. For example, *B. thuringiensis* var. *kurstaki* HD-1 produces a crystal called a delta toxin which is toxic to the larvae of a number of lepidopteran insects. The cloning and expression of this B.t. crystal protein gene in *Escherichia coli* has been described in the published literature (Schnepf, H. E. and Whitely, H. R. [1981]Proc. Natl. Acad. Sci. USA 78:2893-2897). U.S. Pat. No. 4,448,885 and U.S. Pat. No. 4,467,036 both disclose the expression of B.t. crystal protein in *E. coli*. In U.S. Pat. No. 4,467,036 *B. thuringiensis* var. *kurstaki* HD-1 is disclosed as being available from the well-known NRRL culture repository at Peoria, Ill. Its accession number there is NRRL B-3792. *B. thuringiensis* var. *kurstaki* HD-73 is also available from NRRL. Its accession number is NRRL B-4488.

BRIEF SUMMARY OF THE INVENTION

Disclosed and claimed is a novel hybrid toxin gene toxic to lepidopteran insects. This toxin gene has been transferred to a *Pseudomonas fluorescens* host via a plasmid vector.

Specifically, the invention comprises a novel hybrid delta endotoxin gene comprising part of the *B. thuringiensis* var. *kurstaki* HD-73 toxin gene and part of the toxin gene from *B. thuringiensis* var. *kurstaki* strain HD-1. This hybrid gene was inserted into a suitable transfer vector which was then used to transform a *Pseudomonas fluorescens* host. The *P. fluorescens* host can be used as an insecticide active against lepidopteran insects.

More specifically, the subject invention concerns a novel hybrid toxin gene (DNA) encoding a novel protein having activity against lepidopteran insects.

FIG. 1—Nucleotide and amino acid sequences of the hydrid gene and encoded toxin.

DETAILED DISCLOSURE OF THE INVENTION

The novel hybrid toxin gene of the subject invention comprises part of the *B. thuringiensis* var. *kurstaki* HD-73 toxin gene and part of a *B. thuringiensis* var. *kurstaki* strain HD-1 toxin gene. In general, the B.t.k. HD-73 gene portion was initially combined with DNA segments derived from (1) the known *E. coli* plasmid pBR322, (2) a DNA segment conferring the ability to replicate in *Pseudomonas* from the known plasmid pRO1614, and (3) a DNA segment representing the hybrid Tac promoter.

The resulting hybrid gene was contained in a plasmid named pM2,16-11. This plasmid was used to transform a *Pseudomonas fluorescens* microbe to give the transformed strain named MR436.

The toxin gene of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas. Methylophilius, Agrobacterium, Acetobacter, Lactobacillus, Arthrobacter, Azotobacter, Leuconostoc, and Alcaligenes; fungi, particularly yeast, e.g., genera saccharomyces Cryptococcus, Kluyveromyces, Sporobolomyces, Rhodotorula, and Aureobasidium. Of particular interest are such phytosphere bacterial species as *Pseudomonas syringae*, *Pseudomonas fluorescens*, *Serratia marcescens*, *Acetobacter xylinum*, *Agrobacterium tumefaciens*, *Rhodopseudomonas spheroides*, *Xanthomonas campestris*, *Rhizobium melioti*, *Alcaligenes entrophus*, and *Azotobacter vinlandii*; and phytosphere yeast species such as *Rhodotorula rubra*, *R. glutinis*, *R. marina*, *R. aurantiaca*, *Cryptococcus albidus*, *C. diffluens*, *C. laurentii*, *Saccharomyces rosei*, *S. pretoriensis*, *S. cerevisiae*, *Sporobolomyces roseus*, *S. odorus*, *Kluyveromyces veronae*, and *Aureobasidium pollulans*. Of particular interest are the pigmented microorganisms.

A wide variety of ways are available for introducing the B.t. gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototrophy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pR01614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacil laceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B.t.i. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis,* and the like.

The cell will usually be intact and be substantially in the proliferative form when treated, rather than in a spore form, although in some instances spores may be employed.

Treatment of the microbial cell, e.g., a microbe physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

EXAMPLE 1

Construction of Novel Hybrid Toxin Gene and Transformation into *Pseudomonas fluorescens.*

A portion of the B. thuringiensis var. kurstaki HD-73 gene including all of the toxin-encoding DNA from the starting ATG (i.e., start methionine) to the HindIII site was inserted into the Tac-promoted plasmid pKK223-3 (Pharmacia). This was done by making a blunt fusion of this gene just downstream from the ribosome binding site in pKK223-3. This formed plasmid pKK2. Next, the 3' portion of a toxin gene from the Berliner strain of B.t. (DNA 5:305-314 [1986]) was cloned as a SacI to PstI fragment into pKK2/SacI+PstI thus making a recombinant toxin gene in a new plasmid named pKK73BB-9. This gene is of Berliner origin (DNA 5:305-314, 1986) for all sequences beyond (3' to) the SacI site.

Next, pKK73BB-9 was cleaved with NsiI, to release the internal portion of the toxin DNA, treated with bacterial alkaline phosphotose, gel purified and used to subclone a partial HD73-like toxin gene fragment with NsiI termini. The resulting plasmid is called pKKl-73. The HD73-like fragment represents all the DNA sequences between the two NsiI sites commonly found in B.t. toxins. Next, pKKl-73 was cleaved with TthlllI, made blunt with treatment with Klenow fragment plus dNTPs, linkered for BamH1, BamH1 digested, ligated, transformed, and screened to find a plasmid which had deleted the partial tetracycline gene (derived from pKK223-3). This resulted in plasmid pl,123-1. Plasmid pl,123-1 was cleaved with PvuI, treated briefly with Bal 31, made blunt with Klenow and used to clone the similarly blunted tetracycline resistance gene from pBR322 (map positions EcoR1 to Ava1). Screening of tetracycline resistant colonies produced the desired plasmid pl,130-6. This plasmid was linearized by partial digestion with BamH1, gel purified and was used to receive the BamH1 terminated Pseudomonas origin of replication from pR01614. The final result is plasmid pM2,16-11.

Plasmid pM2,16-11 was used to transform a *Pseudomonas fluorescens* using standard transformation procedures.

The HD73-like NsiI fragment, discussed above, was constructed as follows. To the 3' end of the HindIII-terminated partial HD73 gene was added a HindIII to NdeI Berliner-like toxin sequence cloned from *B. thuringiensis* var. kurstaki HD-1.

The above cloning procedures were conducted using standard procedures unless otherwise noted.

The various methods employed in the preparation of the plasmids and transformation of host organisms are well known in the art. These procedures are all described in Maniatis, T., Fritsch, E. F., and Sambrook, J. (1982) *Molecular Cloning: A Laboratory Manual,* Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., or New England Biolabs, Beverly, Mass. The enzymes are used according to the instructions provided by the supplier.

Plasmid pM2,16-11, containing the B.t. toxin gene, can be removed from the transformed host microbe by use of standard well-known procedures. For example, *P. fluorescens* (pM2,16-11) can be subjected to cleared lysate isopcynic density gradient procedures, and the like, to recover pM2,16-11.

A subculture of *P. fluorescens* (pM2,16-11) has been deposited in the permanent collection of the Agricultural Research Service Patent Culture Collection (NRRL), Regional Research Center, 1815 North University Street, Peoria, Ill. 61604 USA on Jan. 15, 1988. The culture was assigned the accession number NRRL B-18292 by the repository. This deposit is available to the public upon the grant of a patent disclosing it. The deposit is also available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing the deposit.

EXAMPLE 2

Insertion of Toxin Gene Into Plants

The novel gene coding for the novel insecticidal toxin, as disclosed herein, can be inserted into plant cells using the Ti plasmid from *Agrobacter tumefaciens.* Plant cells can then be caused to regenerate into plants (Zambryski, P., Joos, H. Gentello, C., Leemans, J., Van Montague, M. and Schell, J. [1983] Cell 32:1033–1043). A particularly useful vector in this regard is pEND4K (Klee, H. J., Yanofsky, M. F. and Nester, E. W. [1985] Bio/Technology 3:637–642). This plasmid can replicate both in plant cells and in bacteria and has multiple cloning sites for passenger genes. The toxin gene, for example, can be inserted into the BamH1 site of pEND4K, propagated in E. coli, and transformed into appropriate plant cells.

EXAMPLE 3

Cloning of Novel Hybrid *B. thuringiensis* Genes Into Baculoviruses

The novel hybrid gene of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G.D., Shoemaker, C. and Miller, L. K. [1984]Mol. Cell. Biol. 4:399–406), and pAC380, described by Smith et al. (Smith, G.E., Summers, M.D. and Fraser, M.J. [1983]Mol Cell. Biol. 3:2156–2165). The gene coding for the novel protein toxin of the invention can be modified with BamH1 linkers at appropriate regions both upstream and downstream from the coding region and inserted into the passenger site of one of the AcNPV vectors.

As disclosed previously, the nucleotide sequence encoding the novel B.t. toxin gene is shown in Table I. The deduced amino acid sequence is shown in Table II.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |

-continued

| Isoleucine (Ile) | ATM | Asparagine (Asn) | AAK |
|---|---|---|---|
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A = adenine
G = guanine
C = cytosine
T = thymine
X = T or C if Y is A or G
X = C if Y is C or T
Y = A, G, C or T if X is C
Y = A or G if X is T
W = C or A if Z is A or G
W = C if Z is C or T
Z = A, G, C or T if W is C
Z = A or G if W is A
QR = TC if S is A, G, C or T; alternatively QR = AG if S is T or C
J = A or G
K = T or C
L = A, T, C or G
M = A, C or T The above shows that the novel amino acid sequence of the B.t. toxin can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or if the structure is altered, the biological activity is retained to some degree.

TABLE 1

|  | 10 | 20 | 30 | 40 | 50 | 60 |
|---|---|---|---|---|---|---|
| 1 | ATGGATAACA | ATCCGAACAT | CAATGAATGC | ATTCCTTATA | ATTGTTTAAG | TAACCCTGAA |
| 61 | GTAGAAGTAT | TAGGTGGAGA | AAGAATAGAA | ACTGGTTACA | CCCCAATCGA | TATTTCCTTG |
| 121 | TCGCTAACGC | AATTTCTTTT | GAGTGAATTT | GTTCCCGGTG | CTGGATTTGT | GTTAGGACTA |
| 181 | GTTGATATAA | TATGGGGAAT | TTTTGGTCCC | TCTCAATGGG | ACGCATTTCT | TGTACAAATT |
| 241 | GAACAGTTAA | TTAACCAAAG | AATAGAAGAA | TTCGCTAGGA | ACCAAGCCAT | TTCTAGATTA |

|  | 310 | 320 | 330 | 340 | 350 | 360 |
|---|---|---|---|---|---|---|
| 301 | GAAGGACTAA | GCAATCTTTA | TCAAATTTAC | GCAGAATCTT | TTAGAGAGTG | GGAAGCAGAT |
| 361 | CCTACTAATC | CAGCATTAAG | AGAAGAGATG | CGTATTCAAT | TCAATGACAT | GAACAGTGCC |
| 421 | CTTACAACCG | CTATTCCTCT | TTTTGCAGTT | CAAAATTATC | AAGTTCCTCT | TTTATCAGTA |
| 481 | TATGTTCAAG | CTGCAAATTT | ACATTTATCA | GTTTTGAGAG | ATGTTTCAGT | GTTTGGACAA |
| 541 | AGGTGGGGAT | TTGATGCCGC | GACTATCAAT | AGTCGTTATA | ATGATTTAAC | TAGGCTTATT |

|  | 610 | 620 | 630 | 640 | 650 | 660 |
|---|---|---|---|---|---|---|
| 601 | GGCAACTATA | CAGATTATGC | TGTACGCTGG | TACAATACGG | GATTAGAACG | TGTATGGGGA |
| 661 | CCGGATTCTA | GAGATTGGGT | AAGGTATAAT | CAATTTAGAA | GAGAATTAAC | ACTAACTGTA |
| 721 | TTAGATATCG | TTGCTCTGTT | CCCGAATTAT | GATAGTAGAA | GATATCCAAT | TCAACAGTT |
| 781 | TCCCAATTAA | CAAGAGAAAT | TTATACAAAC | CCAGTATTAG | AAAATTTTGA | TGGTAGTTTT |
| 841 | CGAGGCTCGG | CTCAGGGCAT | AGAAAGAAGT | ATTAGGAGTC | CACATTTGAT | GGATATACTT |

|  | 910 | 920 | 930 | 940 | 950 | 960 |
|---|---|---|---|---|---|---|
| 901 | AACAGTATAA | CCATCTATAC | GGATGCTCAT | AGGGGTTATT | ATTATTGGTC | AGGGCATCAA |
| 961 | ATAATGGCTT | CTCCTGTAGG | GTTTTCGGGG | CCAGAATTCA | CTTTTCCGCT | ATATGGAACT |
| 1021 | ATGGGAAATG | CAGCTCCACA | ACAACGTATT | GTTGCTCAAC | TAGGTCAGGG | CGTGTATAGA |
| 1081 | ACATTATCGT | CCACTTTATA | TAGAAGACCT | TTTAATATAG | GGATAAATAA | TCAACAACTA |
| 1141 | TCTGTTCTTG | ACGGGACAGA | ATTTGCTTAT | GGAACCTCCT | CAAATTTGCC | ATCCGCTGTA |

|  | 1210 | 1220 | 1230 | 1240 | 1250 | 1260 |
|---|---|---|---|---|---|---|
| 1201 | TACAGAAAAA | GCGGAACGGT | AGATTCGCTG | GATGAAATAC | CGCCACAGAA | TAACAACGTG |
| 1261 | CCACCTAGGC | AAGGATTTAG | TCATCGATTA | AGCCATGTTT | CAATGTTTCG | TTCAGGCTTT |
| 1321 | AGTAATAGTA | GTGTAAGTAT | AATAAGAGCT | CCTATGTTCT | CTTGGATACA | TCGTAGTGCT |
| 1381 | GAATTTAATA | ATATAATTGC | ATCGGATAGT | ATTACTCAAA | TCCCTGCAGT | GAAGGGAAAC |
| 1441 | TTTCTTTTTA | ATGGTTCTGT | AATTTCAGGA | CCAGGATTTA | CTGGTGGGGA | CTTAGTTAGA |

|  | 1510 | 1520 | 1530 | 1540 | 1550 | 1560 |
|---|---|---|---|---|---|---|
| 1501 | TTAAATAGTA | GTGGAAATAA | CATTCAGAAT | AGAGGGTATA | TTGAAGTTCC | AATTCACTTC |
| 1561 | CCATCGACAT | CTACCAGATA | TCGAGTTCGT | GTACGGTATG | CTTCTGTAAC | CCCGATTCAC |
| 1621 | CTCAACGTTA | ATTGGGGTAA | TTCATCCATT | TTTTCCAATA | CAGTACCAGC | TACAGCTACG |
| 1681 | TCATTAGATA | ATCTACAATC | AAGTGATTTT | GGTTATTTTG | AAAGTGCCAA | TGCTTTTACA |
| 1741 | TCTTCATTAG | GTAATATAGT | AGGTGTTAGA | AATTTTAGTG | GGACTGCAGG | AGTGATAATA |

|  | 1810 | 1820 | 1830 | 1840 | 1850 | 1860 |
|---|---|---|---|---|---|---|
| 1801 | GACAGATTTG | AATTTATTCC | AGTTACTGCA | ACACTCGAGG | CTGAATATAA | TCTGGAAAGA |
| 1861 | GCGCAGAAGG | CGGTGAATGC | GCTGTTTACG | TCTACAAACC | AACTAGGGCT | AAAAACAAAT |
| 1921 | GTAACGGATT | ATCATATTGA | TCAAGTGTCC | AATTTAGTTA | CGTATTTATC | GGATGAATTT |
| 1981 | TGTCTGGATG | AAAAGCGAGA | ATTGTCCGAG | AAAGTCAAAC | ATGCGAAGCG | ACTCAGTGAT |
| 2041 | GAACGCAATT | TACTCCAAGA | TTCAAATTTC | AAAGACATTA | ATAGGCAACC | AGAACGTGGG |

|  | 2110 | 2120 | 2130 | 2140 | 2150 | 2160 |

TABLE 1-continued

| | | | | | |
|---|---|---|---|---|---|
| 2101 | TGGGGCGGAA | GTACAGGGAT | TACCATCCAA | GGAGGGGATG | ACGTATTTAA | AGAAAATTAC |
| 2161 | GTCACACTAT | CAGGTACCTT | TGATGAGTGC | TATCCAACAT | ATTTGTATCA | AAAAATCGAT |
| 2221 | GAATCAAAAT | TAAAAGCCTT | TACCCGTTAT | CAATTAAGAG | GGTATATCGA | AGATAGTCAA |
| 2281 | GACTTAGAAA | TCTATTTAAT | TCGCTACAAT | GCAAAACATG | AAACAGTAAA | TGTGCCAGGT |
| 2341 | ACGGGTTCCT | TATGGCCGCT | TTCAGCCCAA | AGTCCAATCG | GAAAGTGTGG | AGAGCCGAAT |

| | | 2410 | 2420 | 2430 | 2440 | 2450 | 2460 |
|---|---|---|---|---|---|---|---|
| 2401 | CGATGCGCGC | CACACCTTGA | ATGGAATCCT | GACTTAGATT | GTTCGTGTAG | GGATGGAGAA |
| 2461 | AAGTGTGCCC | ATCATTCGCA | TCATTTCTCC | TTAGACATTG | ATGTAGGATG | TACAGACTTA |
| 2521 | AATGAGGACC | TAGGTGTATG | GGTGATCTTT | AAGATTAAGA | CGCAAGATGG | GCACGCAAGA |
| 2581 | CTAGGGAATC | TAGAGTTTCT | CGAAGAGAAA | CCATTAGTAG | GAGAAGCGCT | AGCTCGTGTG |
| 2641 | AAAAGAGCGG | AGAAAAAATG | GAGAGACAAA | CGTGAAAAAT | TGGAATGGGA | AACAAATATC |

| | | 2710 | 2720 | 2730 | 2740 | 2750 | 2760 |
|---|---|---|---|---|---|---|---|
| 2701 | GTTTATAAAG | AGGCAAAAGA | ATCTGTAGAT | GCTTTATTTG | TAAACTCTCA | ATATGATCAA |
| 2761 | TTACAAGCGG | ATACGAATAT | TGCCATGATT | CATGCGGCAG | ATAAACGTGT | TCATAGCATT |
| 2821 | CGAGAAGCTT | ATCTGCCTGA | GCTGTCTGTG | ATTCCGGCTG | TCAATGCGGC | TATTTTTGAA |
| 2881 | GAATTAGAAG | GGCGTATTTT | CACTGCATTC | TCCCTATATG | ATGCGAGAAA | TGTCATTAAA |
| 2941 | AATGGTGATT | TTAATAATGG | CTTATCCTGC | TGGAACGTGA | AAGGGCATGT | AGATGTAGAA |

| | | 3010 | 3020 | 3030 | 3040 | 3050 | 3060 |
|---|---|---|---|---|---|---|---|
| 3001 | GAACAAAACA | ACCACCGTTC | GGTCCTTGTT | GTTCCGGAAT | GGGAAGCAGA | AGTGTCACAA |
| 3061 | GAAGTTCGTG | TCTGTCCGGG | TCGTGGCTAT | ATCCTTCGTG | TCACGCGTA | CAAGGAGGGA |
| 3121 | TATGGAGAAG | GTTGCGTAAC | CATTCATGAG | ATCGAGAACA | ATACAGACGA | ACTGAAGTTT |
| 3181 | AGCAACTGTG | TAGAAGAGGA | AGTATATCCA | AACAACACGG | TAACGTGTAA | TGATTATACT |
| 3241 | GCGACTCAAG | AAGAATATGA | GGCTACGTAC | ACTTCTCGTA | ATCGAGGATA | TGACGGAGCC |

| | | 3310 | 3320 | 3330 | 3340 | 3350 | 3360 |
|---|---|---|---|---|---|---|---|
| 3301 | TATGAAAGCA | ATTCTTCTGT | ACCAGCTGAT | TATGCATCAG | CCTATGAAGA | AAAAGCATAT |
| 3361 | ACAGATGGAC | GAAGAGACAA | TCCTTGTGAA | TCTAACAGAG | GATATGGGGA | TTACACACCA |
| 3421 | CTACCAGCTG | GCTATGTGAC | AAAAGAATTA | GAGTACTTCC | CAGAAACCGA | TAAGGTATGG |
| 3481 | ATTGAGATCG | GAGAAACGGA | AGGAACATTC | ATCGTGGACA | GCGTGGAATT | ACTTCTTATG |
| 3541 | GAGGAA<u>TAA</u>T* | ATATGCTTTA | AAATGTAAGG | TGTGCAAATA | AAGAATGATT | ACTGACTTGT |

| | | 3610 | 3620 | 3630 | 3640 | 3650 | 3660 |
|---|---|---|---|---|---|---|---|
| 3601 | ATTGACAGAT | AAATAAGGAA | ATTTTTATAT | GAATAAAAAA | CGGGCATCAC | TCTTAAAAGA |
| 3661 | ATGATGTCCG | TTTTTTGTAT | GATTTAACGA | GTGATATTTA | AATGTTTTTT | TGCGAAGG |

*stop codon

TABLE 2

| | | | | 5 | | | | | 10 | | | | | 15 | | | | | 20 |
|---|---|---|---|---|---|---|---|---|---|---|---|---|---|---|---|---|---|---|---|
| Met | Asp | Asn | Asn | Pro | Asn | Ile | Asn | Glu | Cys | Ile | Pro | Tyr | Asn | Cys | Leu | Ser | Asn | Pro | Glu |
| | | | | 25 | | | | | 30 | | | | | 35 | | | | | 40 |
| Val | Glu | Val | Leu | Gly | Gly | Glu | Arg | Ile | Glu | Thr | Gly | Tyr | Thr | Pro | Ile | Asp | Ile | Ser | Leu |
| | | | | 45 | | | | | 50 | | | | | 55 | | | | | 60 |
| Ser | Leu | Thr | Gln | Phe | Leu | Leu | Ser | Glu | Phe | Val | Pro | Gly | Ala | Gly | Phe | Val | Leu | Gly | Leu |
| | | | | 65 | | | | | 70 | | | | | 75 | | | | | 80 |
| Val | Asp | Ile | Ile | Trp | Gly | Ile | Phe | Gly | Pro | Ser | Gln | Trp | Asp | Ala | Phe | Leu | Val | Gln | Ile |
| | | | | 85 | | | | | 90 | | | | | 95 | | | | | 100 |
| Glu | Gln | Leu | Ile | Asn | Gln | Arg | Ile | Glu | Glu | Phe | Ala | Arg | Asn | Gln | Ala | Ile | Ser | Arg | Leu |
| | | | | 105 | | | | | 110 | | | | | 115 | | | | | 120 |
| Glu | Gly | Leu | Ser | Asn | Leu | Tyr | Gln | Ile | Tyr | Ala | Glu | Ser | Phe | Arg | Glu | Trp | Glu | Ala | Asp |
| | | | | 125 | | | | | 130 | | | | | 135 | | | | | 140 |
| Pro | Thr | Asn | Pro | Ala | Leu | Arg | Glu | Glu | Met | Arg | Ile | Gln | Phe | Asn | Asp | Met | Asn | Ser | Ala |
| | | | | 145 | | | | | 150 | | | | | 155 | | | | | 160 |
| Leu | Thr | Thr | Ala | Ile | Pro | Leu | Phe | Ala | Val | Gln | Asn | Tyr | Gln | Val | Pro | Leu | Leu | Ser | Val |
| | | | | 165 | | | | | 170 | | | | | 175 | | | | | 180 |
| Tyr | Val | Gln | Ala | Ala | Asn | Leu | His | Leu | Ser | Val | Leu | Arg | Asp | Val | Ser | Val | Phe | Gly | Gln |
| | | | | 185 | | | | | 190 | | | | | 195 | | | | | 200 |
| Arg | Trp | Gly | Phe | Asp | Ala | Ala | Thr | Ile | Asn | Ser | Arg | Tyr | Asn | Asp | Leu | Thr | Arg | Leu | Ile |
| | | | | 205 | | | | | 210 | | | | | 215 | | | | | 220 |
| Gly | Asn | Tyr | Thr | Asp | Tyr | Ala | Val | Arg | Trp | Tyr | Asn | Thr | Gly | Leu | Glu | Arg | Val | Trp | Gly |
| | | | | 225 | | | | | 230 | | | | | 235 | | | | | 240 |
| Pro | Asp | Ser | Arg | Asp | Trp | Val | Arg | Tyr | Asn | Gln | Phe | Arg | Arg | Glu | Leu | Thr | Leu | Thr | Val |
| | | | | 245 | | | | | 250 | | | | | 255 | | | | | 260 |
| Leu | Asp | Ile | Val | Ala | Leu | Phe | Pro | Asn | Tyr | Asp | Ser | Arg | Arg | Tyr | Pro | Ile | Arg | Thr | Val |
| | | | | 265 | | | | | 270 | | | | | 275 | | | | | 280 |

TABLE 2-continued

| | | | | | | | | | | | | | | | | | | |
|---|---|---|---|---|---|---|---|---|---|---|---|---|---|---|---|---|---|---|
| Ser | Gln | Leu | Thr | Arg | Glu | Ile | Tyr | Thr | Asn | Pro | Val | Leu | Glu | Asn | Phe | Asp | Gly | Ser | Phe |
| Arg | Gly | Ser | Ala | 285 Gln | Gly | Ile | Glu | Arg | 290 Ser | Ile | Arg | Ser | Pro | 295 His | Leu | Met | Asp | Ile | 300 Leu |
| Asn | Ser | Ile | Thr | 305 Ile | Tyr | Thr | Asp | Ala | 310 His | Arg | Gly | Tyr | Tyr | 315 Tyr | Trp | Ser | Gly | His | 320 Gln |
| Ile | Met | Ala | Ser | 325 Pro | Val | Gly | Phe | Ser | 330 Gly | Pro | Glu | Phe | Thr | 335 Phe | Pro | Leu | Tyr | Gly | 340 Thr |
| Met | Gly | Asn | Ala | 345 Ala | Pro | Gln | Gln | Arg | 350 Ile | Val | Ala | Gln | Leu | 355 Gly | Gln | Gly | Val | Tyr | 360 Arg |
| Thr | Leu | Ser | Ser | 365 Thr | Leu | Tyr | Arg | Arg | 370 Pro | Phe | Asn | Ile | Gly | 375 Ile | Asn | Asn | Gln | Gln | 380 Leu |
| Ser | Val | Leu | Asp | 385 Gly | Thr | Glu | Phe | Ala | 390 Tyr | Gly | Thr | Ser | Ser | 395 Asn | Leu | Pro | Ser | Ala | 400 Val |
| Tyr | Arg | Lys | Ser | 405 Gly | Thr | Val | Asp | Ser | 410 Leu | Asp | Glu | Ile | Pro | 415 Pro | Gln | Asn | Asn | Asn | 420 Val |
| Pro | Pro | Arg | Gln | 425 Gly | Phe | Ser | His | Arg | 430 Leu | Ser | His | Val | Ser | 435 Met | Phe | Arg | Ser | Gly | 440 Phe |
| Ser | Asn | Ser | Ser | 445 Val | Ser | Ile | Ile | Arg | 450 Ala | Pro | Met | Phe | Ser | 455 Trp | Ile | His | Arg | Ser | 460 Ala |
| Glu | Phe | Asn | Asn | 465 Ile | Ile | Ala | Ser | Asp | 470 Ser | Ile | Thr | Gln | Ile | 475 Pro | Ala | Val | Lys | Gly | 480 Asn |
| Phe | Leu | Phe | Asn | 485 Gly | Ser | Val | Ile | Ser | 490 Gly | Pro | Gly | Phe | Thr | 495 Gly | Gly | Asp | Leu | Val | 500 Arg |
| Leu | Asn | Ser | Ser | 505 Gly | Asn | Asn | Ile | Gln | 510 Asn | Arg | Gly | Tyr | Ile | 515 Glu | Val | Pro | Ile | His | 520 Phe |
| Pro | Ser | Thr | Ser | 525 Thr | Arg | Tyr | Arg | Val | 530 Arg | Val | Arg | Tyr | Ala | 535 Ser | Val | Thr | Pro | Ile | 540 His |
| Leu | Asn | Val | Asn | 545 Trp | Gly | Asn | Ser | Ser | 550 Ile | Phe | Ser | Asn | Thr | 555 Val | Pro | Ala | Thr | Ala | 560 Thr |
| Ser | Leu | Asp | Asn | 565 Leu | Gln | Ser | Ser | Asp | 570 Phe | Gly | Tyr | Phe | Glu | 575 Ser | Ala | Asn | Ala | Phe | 580 Thr |
| Ser | Ser | Leu | Gly | 585 Asn | Ile | Val | Gly | Val | 590 Arg | Asn | Phe | Ser | Gly | 595 Thr | Ala | Gly | Val | Ile | 600 Ile |
| Asp | Arg | Phe | Glu | 605 Phe | Ile | Pro | Val | Thr | 610 Ala | Thr | Leu | Glu | Ala | 615 Glu | Tyr | Asn | Leu | Glu | 620 Arg |
| Ala | Gln | Lys | Ala | 625 Val | Asn | Ala | Leu | Phe | 630 Thr | Ser | Thr | Asn | Gln | 635 Leu | Gly | Leu | Lys | Thr | 640 Asn |
| Val | Thr | Asp | Tyr | 645 His | Ile | Asp | Gln | Val | 650 Ser | Asn | Leu | Val | Thr | 655 Tyr | Leu | Ser | Asp | Glu | 660 Phe |
| Cys | Leu | Asp | Glu | 665 Lys | Arg | Glu | Leu | Ser | 670 Glu | Lys | Val | Lys | His | 675 Ala | Lys | Arg | Leu | Ser | 680 Asp |
| Glu | Arg | Asn | Leu | 685 Leu | Gln | Asp | Ser | Asn | 690 Phe | Lys | Asp | Ile | Asn | 695 Arg | Gln | Pro | Glu | Arg | 700 Gly |
| Trp | Gly | Gly | Ser | 705 Thr | Gly | Ile | Thr | Ile | 710 Gln | Gly | Gly | Asp | Asp | 715 Val | Phe | Lys | Glu | Asn | 720 Tyr |
| Val | Thr | Leu | Ser | 725 Gly | Thr | Phe | Asp | Glu | 730 Cys | Tyr | Pro | Thr | Tyr | 735 Leu | Tyr | Gln | Lys | Ile | 740 Asp |
| Glu | Ser | Lys | Leu | 745 Lys | Ala | Phe | Thr | Arg | 750 Tyr | Gln | Leu | Arg | Gly | 755 Tyr | Ile | Glu | Asp | Ser | 760 Gln |
| Asp | Leu | Glu | Ile | 765 Tyr | Leu | Ile | Arg | Tyr | 770 Asn | Ala | Lys | His | Glu | 775 Thr | Val | Asn | Val | Pro | 780 Gly |
| Thr | Gly | Ser | Leu | 785 Trp | Pro | Leu | Ser | Ala | 790 Gln | Ser | Pro | Ile | Gly | 795 Lys | Cys | Gly | Glu | Pro | 800 Asn |
| Arg | Cys | Ala | Pro | 805 His | Leu | Glu | Trp | Asn | 810 Pro | Asp | Leu | Asp | Cys | 815 Ser | Cys | Arg | Asp | Gly | 820 Glu |

TABLE 2-continued

|     |     |     |     | 825 |     |     |     |     | 830 |     |     |     |     | 835 |     |     |     |     | 840 |
| --- | --- | --- | --- | --- | --- | --- | --- | --- | --- | --- | --- | --- | --- | --- | --- | --- | --- | --- | --- |
| Lys | Cys | Ala | His | His | Ser | His | His | Phe | Ser | Leu | Asp | Ile | Asp | Val | Gly | Cys | Thr | Asp | Leu |
|     |     |     |     | 845 |     |     |     |     | 850 |     |     |     |     | 855 |     |     |     |     | 860 |
| Asn | Glu | Asp | Leu | Gly | Val | Trp | Val | Ile | Phe | Lys | Ile | Lys | Thr | Gln | Asp | Gly | His | Ala | Arg |
|     |     |     |     | 865 |     |     |     |     | 870 |     |     |     |     | 875 |     |     |     |     | 880 |
| Leu | Gly | Asn | Leu | Glu | Phe | Leu | Glu | Glu | Lys | Pro | Leu | Val | Gly | Glu | Ala | Leu | Ala | Arg | Val |
|     |     |     |     | 885 |     |     |     |     | 890 |     |     |     |     | 895 |     |     |     |     | 900 |
| Lys | Arg | Ala | Glu | Lys | Lys | Trp | Arg | Asp | Lys | Arg | Glu | Lys | Leu | Glu | Trp | Glu | Thr | Asn | Ile |
|     |     |     |     | 905 |     |     |     |     | 910 |     |     |     |     | 915 |     |     |     |     | 920 |
| Val | Tyr | Lys | Glu | Ala | Lys | Glu | Ser | Val | Asp | Ala | Leu | Phe | Val | Asn | Ser | Gln | Tyr | Asp | Gln |
|     |     |     |     | 925 |     |     |     |     | 930 |     |     |     |     | 935 |     |     |     |     | 940 |
| Leu | Gln | Ala | Asp | Thr | Asn | Ile | Ala | Met | Ile | His | Ala | Ala | Asp | Lys | Arg | Val | His | Ser | Ile |
|     |     |     |     | 945 |     |     |     |     | 950 |     |     |     |     | 955 |     |     |     |     | 960 |
| Arg | Glu | Ala | Tyr | Leu | Pro | Glu | Leu | Ser | Val | Ile | Pro | Ala | Val | Asn | Ala | Ala | Ile | Phe | Glu |
|     |     |     |     | 965 |     |     |     |     | 970 |     |     |     |     | 975 |     |     |     |     | 980 |
| Glu | Leu | Glu | Gly | Arg | Ile | Phe | Thr | Ala | Phe | Ser | Leu | Tyr | Asp | Ala | Arg | Asn | Val | Ile | Lys |
|     |     |     |     | 985 |     |     |     |     | 990 |     |     |     |     | 995 |     |     |     |     | 1000 |
| Asn | Gly | Asp | Phe | Asn | Asn | Gly | Leu | Ser | Cys | Trp | Asn | Val | Lys | Gly | His | Val | Asp | Val | Glu |
|     |     |     |     | 1005 |     |     |     |     | 1010 |     |     |     |     | 1015 |     |     |     |     | 1020 |
| Glu | Gln | Asn | Asn | His | Arg | Ser | Val | Leu | Val | Val | Pro | Glu | Trp | Glu | Ala | Glu | Val | Ser | Gln |
|     |     |     |     | 1025 |     |     |     |     | 1030 |     |     |     |     | 1035 |     |     |     |     | 1040 |
| Glu | Val | Arg | Val | Cys | Pro | Gly | Arg | Gly | Tyr | Ile | Leu | Arg | Val | Thr | Ala | Tyr | Lys | Glu | Gly |
|     |     |     |     | 1045 |     |     |     |     | 1050 |     |     |     |     | 1055 |     |     |     |     | 1060 |
| Tyr | Gly | Glu | Gly | Cys | Val | Thr | Ile | His | Glu | Ile | Glu | Asn | Asn | Thr | Asp | Glu | Leu | Lys | Phe |
|     |     |     |     | 1065 |     |     |     |     | 1070 |     |     |     |     | 1075 |     |     |     |     | 1080 |
| Ser | Asn | Cys | Val | Glu | Glu | Glu | Val | Tyr | Pro | Asn | Asn | Thr | Val | Thr | Cys | Asn | Asp | Tyr | Thr |
|     |     |     |     | 1085 |     |     |     |     | 1090 |     |     |     |     | 1095 |     |     |     |     | 1100 |
| Ala | Thr | Gln | Glu | Glu | Tyr | Glu | Ala | Thr | Tyr | Thr | Ser | Arg | Asn | Arg | Gly | Tyr | Asp | Gly | Ala |
|     |     |     |     | 1105 |     |     |     |     | 1110 |     |     |     |     | 1115 |     |     |     |     | 1120 |
| Tyr | Glu | Ser | Asn | Ser | Ser | Val | Pro | Ala | Asp | Tyr | Ala | Ser | Ala | Tyr | Glu | Glu | Lys | Ala | Tyr |
|     |     |     |     | 1125 |     |     |     |     | 1130 |     |     |     |     | 1135 |     |     |     |     | 1140 |
| Thr | Asp | Gly | Arg | Arg | Asp | Asn | Pro | Cys | Glu | Ser | Asn | Arg | Gly | Tyr | Gly | Asp | Tyr | Thr | Pro |
|     |     |     |     | 1145 |     |     |     |     | 1150 |     |     |     |     | 1155 |     |     |     |     | 1160 |
| Leu | Pro | Ala | Gly | Tyr | Val | Thr | Lys | Glu | Leu | Glu | Tyr | Phe | Pro | Glu | Thr | Asp | Lys | Val | Trp |
|     |     |     |     | 1165 |     |     |     |     | 1170 |     |     |     |     | 1175 |     |     |     |     | 1180 |
| Ile | Glu | Ile | Gly | Glu | Thr | Glu | Gly | Thr | Phe | Ile | Val | Asp | Ser | Val | Glu | Leu | Leu | Leu | Met |
| Glu | Glu | *** |     |     |     |     |     |     |     |     |     |     |     |     |     |     |     |     |     |

TABLE 3

| Pos | AA | Codon | Pos | AA | Codon | Pos | AA | Codon | Pos | AA | Codon |
|---|---|---|---|---|---|---|---|---|---|---|---|
| 1 | Met | ATG | 2 | Asp | GAT | 3 | Asn | AAC | 4 | Asn | AAT |
| 5 | Pro | CCG | 6 | Asn | AAC | 7 | Ile | ATC | 8 | Asn | AAT |
| 9 | Glu | GAA | 10 | Cys | TGC | 11 | Ile | ATT | 12 | Pro | CTT |
| 13 | Tyr | TAT | 14 | Asn | AAT | 15 | Cys | TGT | 16 | Leu | TTA |
| 17 | Ser | AGT | 18 | Asn | AAC | 19 | Pro | CCT | 20 | Glu | GAA |
| 21 | Val | GTA | 22 | Glu | GAA | 23 | Val | GTA | 24 | Leu | TTA |
| 25 | Gly | GGT | 26 | Gly | GGA | 27 | Glu | GAA | 28 | Arg | AGA |
| 29 | Ile | ATA | 30 | Glu | GAA | 31 | Thr | ACT | 32 | Tyr | TAC |
| 33 | Gly | GGT | 34 | Gly | GGA | 35 | Pro | CCA | 36 | Ile | ATC |
| 37 | Asp | GAT | 38 | Ile | ATT | 39 | Ser | TCC | 40 | Leu | TTG |
| 41 | Ser | TCG | 42 | Leu | CTA | 43 | Thr | ACG | 44 | Val | GTA |
| 45 | Phe | TTT | 46 | Leu | CTT | 47 | Leu | TTG | 48 | Ser | AGT |
| 49 | Phe | TTT | 50 | Phe | TTT | 51 | Pro | CCC | 52 | Gly | GGT |
| 53 | Pro | CCC | 54 | Gly | GGA | 55 | Gly | GGA | 56 | Val | GTG |
| 57 | Phe | TTT | 58 | Leu | TTA | 59 | Gly | GGA | 60 | Leu | CTA |
| 61 | Val | GTT | 62 | Asp | GAT | 63 | Thr | ACG | 64 | Ile | ATA |
| 65 | Trp | TGG | 66 | Ile | ATT | 67 | Ile | ATT | 68 | Arg | AGA |
| 69 | Ile | ATT | 70 | Pro | CCC | 71 | Ser | TCT | 72 | Trp | TGG |
| 73 | Arg | AGG | 74 | Ala | GCT | 75 | Ala | GCA | 76 | Phe | TTT |
| 77 | Phe | TTT | 78 | Leu | CTT | 79 | Gln | CAA | 80 | Ile | ATT |
| 81 | Glu | GAA | 82 | Gln | CAG | 83 | Ile | ATA | 84 | Leu | TTA |
| 85 | Asn | AAC | 86 | Ile | ATT | 87 | Phe | TTT | 88 | Gln | CAA |
| 89 | Gly | GGT | 90 | Glu | GAA | 91 | Pro | CCC | 92 | Gln | CAA |
| 93 | Asp | GAC | 94 | Asp | GAT | 95 | Gln | CAA | 96 | Phe | TTT |
| 97 | Phe | TTT | 98 | Ala | GCC | 99 | Val | GTA | 100 | Leu | TTA |
| 101 | Glu | GAA | 102 | Gly | GGA | 103 | Leu | TTA | 104 | Leu | CTA |
| 105 | Asn | AAT | 106 | Ile | ATA | 107 | Gln | CAA | 108 | Ala | GCT |
| 109 | Arg | AGG | 110 | Tyr | TAC | 111 | Tyr | TAT | 112 | Phe | TTT |
| 113 | Ala | GCA | 114 | Glu | GAG | 115 | Arg | AGA | 116 | Asn | AAC |
| 117 | Leu | CTT | 118 | Gln | CAA | 119 | Val | GTA | 120 | Asp | GAT |
| 121 | Glu | GAA | 122 | Gly | GGA | 123 | Leu | TTA | 124 | Leu | CTA |
| 125 | Ala | GCA | 126 | Arg | AGA | 127 | Tyr | TAT | 128 | Glu | GAA |
| 129 | Ser | TCT | 130 | Met | ATG | 131 | Arg | CGT | 132 | Ile | ATT |
| 133 | Gln | CAA | 134 | Ser | AGT | 135 | Asn | AAT | 136 | Phe | TTC |
| 137 | Ile | ATT | 138 | Trp | TGG | 139 | Met | ATG | 140 | Ala | GCC |
| 141 | Pro | CCT | 142 | Thr | ACT | 143 | Ala | GCT | 144 | Ala | GCT |
| 145 | Ile | ATT | 146 | His | CAT | 147 | Ile | ATC | 148 | Asn | AAT |
| 149 | Asn | AAT | 150 | Val | GTT | 151 | Ser | AGT | 152 | Tyr | TAT |
| 153 | Arg | AGA | 154 | Gln | CAA | 155 | Val | GTT | 156 | Asp | GAT |
| 157 | Pro | CCT | 158 | Met | ATG | 159 | Leu | TTA | 160 | Val | GTA |
| 161 | Leu | CTT | 162 | Thr | ACC | 163 | Ala | GCT | 164 | Ala | GCT |
| 165 | Ala | GCA | 166 | Leu | TTA | 167 | Leu | TTA | 168 | Leu | CTT |
| 169 | Arg | AGA | 170 | Ser | TCA | 171 | Ser | TCA | 172 | Leu | TTA |
| 173 | Tyr | TAT | 174 | Arg | AGA | 175 | Val | GTT | 176 | Val | GTG |
| 177 | Val | GTG | 178 | Ser | AGT | 179 | Gly | GGA | 180 | Gln | CAA |
| 181 | Tyr | TAT | 182 | Arg | AGG | 183 | Asp | GAT | 184 | Phe | TTT |
| 185 | Asp | GAT | 186 | Asp | GAT | 187 | Ala | GCG | 188 | Ala | GCT |
| 189 | Asn | AAT | 190 | Asn | AAT | 191 | Ile | ATC | 192 | Thr | ACT |
| 193 | Arg | CGT | 194 | Tyr | TAT | 195 | Asp | GAT | 196 | Ser | AGT |
| 197 | Leu | TTA | 198 | Arg | CGT | 199 | Leu | CTT | 200 | Ile | ATT |
| 201 | Gly | GGC | 202 | Asn | AAC | 203 | Tyr | TAT | 204 | Thr | ACA |
| 205 | Asp | GAT | 206 | Tyr | TAT | 207 | Ala | GCT | 208 | Ala | GCT |
| 209 | Val | GTA | 210 | Trp | TGG | 211 | Arg | CGC | 212 | Asn | AAT |
| 213 | Thr | ACG | 214 | Arg | AGA | 215 | Leu | TTA | 216 | Arg | CGT |
| 217 | Thr | ACT | 218 | Arg | AGG | 219 | Val | GTA | 220 | Gly | GGA |
| 221 | Pro | CCG | 222 | Asp | GAT | 223 | Ser | TCT | 224 | Arg | AGA |
| 225 | Asp | GAT | 226 | Tyr | TAT | 227 | Tyr | TAT | 228 | Arg | AGG |
| 229 | Asn | AAT | 230 | Asn | AAT | 231 | Gln | CAA | 232 | Gln | CAA |
| 233 | Glu | GAA | 234 | Arg | AGA | 235 | Glu | GAA | 236 | Arg | AGA |
| 237 | Arg | AGA | 238 | Phe | TTT | 239 | Val | GTA | 240 | Val | GTA |
| 241 | Leu | TTA | 242 | Val | GTT | 243 | Ala | GCT | 244 | Arg | AGA |
| 245 | Ala | GCT | 246 | Asp | GAT | 247 | Phe | TTC | 248 | Pro | CCG |
| 249 | Asn | AAT | 250 | Tyr | TAT | 251 | Asp | GAT | 252 | Gln | CAA |
| 253 | Ile | ATT | 254 | Leu | CTA | 255 | Tyr | TAT | 256 | Pro | CCA |
| 257 | Thr | ACT | 258 | Arg | CGA | 259 | Leu | CTA | 260 | Val | GTT |

TABLE 3-continued

| | | | | | | | | | | | | | | |
|---|---|---|---|---|---|---|---|---|---|---|---|---|---|---|
| Ser TCC | Gln CAA | Leu TTA | Thr ACA | Arg AGA | Glu GAA | Ile ATT | Tyr TAT | Thr ACA | Asn AAC | Phe TTT | Val GTA | Leu TTA | Glu GAA | Phe TTT |
| | | | | 285 | | | | | 290 | | | | | 295 |
| Arg CGA | Gly GGC | Ser TCG | Ala GCT | Gln CAG | Gly GGC | Ile ATA | Glu GAA | Arg AGA | Ser AGT | Leu TTG | Arg AGG | Ser AGT | Asp GAT | Leu CTT |
| | | | | | | | | | | | | | | 300 |
| Asn AAC | Ser AGT | Ile ATA | Thr ACC | Ile ATC | Tyr TAT | Thr ACG | Asp GAT | Gly GGT | His CAT | Trp TGG | Met ATG | Ser TCA | Gly GGG | Gln CAA |
| | | | | 305 | | | | | 310 | | | | | 315 |
| Ile ATA | Met ATG | Ala GCT | Ser TCT | Pro CCT | Phe TTT | Thr ACG | Gly GGG | Arg AGG | Gly GGG | Pro CCG | Ser TCA | Leu CTA | Tyr TAT | Thr ACT |
| | | | | 320 | | | | | 325 | | | | | 330 |
| Met ATG | Gly GGA | Ala GCT | Ala GCA | Pro CCT | Val GTA | Gln CAA | Phe TTT | Arg AGA | Arg CGT | Gln CAG | Thr ACA | Gly GGT | His CAT | Gly GGA |
| | | | | 335 | | | | | 340 | | | | | 345 |
| Thr ACA | Leu TTA | Ser TCC | Asp GAC | Thr ACT | Thr ACA | Arg CGT | Arg AGA | Ile ATA | Tyr TAT | Leu CTA | Ile ATA | Leu CTA | Gly GGG | Ala GCT |
| | | | | 350 | | | | | 355 | | | | | 360 |
| Ser TCT | Val GTT | Lys AAA | Ser AGC | Gly GGG | Gly GGG | Arg AGA | Phe TTT | Glu GAA | Val GTA | Ile ATA | Ser TCC | Phe TTC | Gly GGA | Asn AAT |
| | | | | 365 | | | | | 370 | | | | | 375 |
| Tyr TAC | Arg AGA | Leu CTT | Gly GGA | Gly GGA | Phe TTT | Arg AGA | Arg AGA | Glu GAA | Asp GAT | Leu CTA | Ser TCA | Ile ATA | Ala GCA | Thr ACC |
| | | | | 380 | | | | | 385 | | | | | 390 |
| Pro CCA | Ser AGT | Ala GCT | Gln CAA | Arg CGA | Arg AGA | Ala GCT | Ala GCT | Ser TCC | Ile ATA | Glu GAA | Ser TCA | Pro CCG | Gly GGC | Ala GCA |
| | | | | 395 | | | | | 400 | | | | | 405 |
| Ser AGT | Asn AAT | Ser AGT | Ser AGT | Val GTA | Ile ATA | Arg AGA | Arg CGA | Thr ACT | Arg AGA | Pro CCT | Ser TCA | Met ATG | Asn AAT | Phe TTT |
| | | | | 410 | | | | | 415 | | | | | 420 |
| Glu GAA | Phe TTT | Lys AAA | Gln CAA | Ala GCT | Ile ATA | Ala GCA | Asp GAT | Ser TCG | Gln CAG | Thr ACT | Ile ATC | Ala GCA | Gly GGG | Val GTG |
| | | | | 425 | | | | | 430 | | | | | 435 |
| Phe TTT | Leu CTT | Asn AAT | Asn AAT | Ile ATA | Ser AGT | Val GTA | Asn AAC | Phe TTT | Pro CCA | Arg CGT | His CAT | Trp TGG | Ser AGT | Phe TTT |
| | | | | 440 | | | | | 445 | | | | | 450 |
| Leu TTA | Asn AAT | Ser AGT | Ser AGT | Asn AAT | Gly GGA | Pro CCA | Asn AAT | Arg CGT | Lys AAG | Leu TTA | Ile ATT | Pro CCA | His CAC | Ile ATA |
| | | | | 455 | | | | | 460 | | | | | 465 |
| Pro | Ser | Thr | Ser | Thr | Arg | Tyr | Arg | Val | Arg | Ala | Tyr | Val | Ser | Ile |
| | | | | | | | | | | | | | | His |

TABLE 3-continued

| | | | | | | | | | | | | | | | | | | | |
|---|---|---|---|---|---|---|---|---|---|---|---|---|---|---|---|---|---|---|---|
| CCA | TCG | ACA | TCT | ACC | AGA | TAT | CGA | GTT | CGT | GTA | CGG | TAT | GCT | TCT | GTA | ACC | CCG | ATT | CAC |
| Leu CTC | Asn AAC | Val GTT | Asn AAT | 545 Trp TGG | Gly GGT | Asn AAT | Ser TCA | Ser TCC | 550 Ile ATT | Phe TTT | Ser TCC | Asn AAT | Thr ACA | 555 Val GTA | Pro CCA | Ala GCT | Thr ACA | 560 Thr ACG | |
| Ser TCA | Leu TTA | Asp GAT | Asn AAT | 565 Leu CTA | Gln CAA | Ser TCA | Ser AGT | Asp GAT | 570 Phe TTT | Gly GGT | Tyr TAT | Phe TTT | Glu GAA | 575 Ser AGT | Ala GCC | Asn AAT | Ala GCT | 580 Thr ACA | |
| Ser TCT | Asn AAT | Gly GGT | Gly GGT | 585 Asn AAT | Ile ATA | Val GTA | Gly GGT | Gly GGT | 590 Arg AGA | Asn AAT | Phe TTT | Ser AGT | Gly GGG | 595 Thr ACT | Ala GCA | Gly GGA | Val GTG | 600 Ile ATA | |
| Asp GAC | Arg AGA | Phe TTT | Glu GAA | 605 Phe TTT | Ile ATT | Pro CCA | Ala GCG | Asp GAT | 601 Ala GCA | Thr ACA | Leu CTC | Glu GAG | Ala GCT | 615 Glu GAA | Tyr TAT | Asn AAT | Leu CTG | 620 Arg AGA | |
| Ala GCG | Gln CAG | Lys AAG | Ala GCG | 625 Val GTG | Asn AAT | Ala GCG | Asp GAT | Glu GAA | 630 Thr ACG | Leu CTG | Val GTC | Ser AGT | Gln CAA | 635 Leu CTA | Gly GGG | Leu CTA | Lys AAA | 640 Asn AAT | |
| Val GTA | Thr ACG | Asp GAT | Tyr TAT | 645 His CAT | Ile ATT | Asp GAT | Leu CTG | Ser TCC | 650 Ser TCC | Asn AAT | Asn AAC | Leu TTA | Thr ACG | 655 Tyr TAT | Leu TTA | Ser TCG | Asp GAT | 660 Phe TTT | |
| Cys TGT | Leu CTG | Lys AAG | Ala GCG | 665 Lys AAG | Arg CGA | Phe TTT | Ser TCA | Asn AAT | 670 Glu GAG | Leu TTG | Val GTT | His CAT | Thr ACG | 675 Ala GCG | Lys AAG | Arg CGA | Leu CTC | 680 Asp GAT | |
| Glu GAA | Arg CGC | Asp GAT | Leu TTA | 685 Leu CTC | Ile ATT | Gln CAA | Asn AAT | Ile ATC | 690 Phe TTC | Asp GAC | Lys AAA | Asn AAT | Gly GGG | 695 Arg AGG | Pro CCA | Lys AAA | Glu GAA | 700 Gly GGG | |
| Trp TGG | Gly GGC | Asn AAT | Ser AGT | 705 Thr ACA | Gly GGG | Thr ACC | Ser TCA | Glu GAG | 710 Gln CAA | Pro CCA | Lys AAA | Asp GAC | Gly GGG | 715 Val GTA | Lys AAA | Gln CAA | Leu CTC | 720 Tyr TAC | |
| Val GTC | Thr ACA | Leu CTA | Ser TCA | 725 Gly GGT | Ala GCC | Ala GCC | Thr ACC | Arg CGT | 730 Cys TGC | Pro CCA | Tyr TAT | Tyr TAT | Phe TTT | 735 Leu TTG | Gln CAA | Glu GAA | Lys AAA | 740 Asp GAT | |
| Glu GAA | Ser TCA | Lys AAA | Leu TTA | 745 Lys AAA | Leu TTA | Phe TTT | Thr ACC | Asp GAT | 750 Tyr TAT | Gln CAA | Lys AAA | Thr ACA | Gly GGG | 755 Tyr TAT | Gln CAA | Gln CAA | Asp GAT | 760 Gln CAA | |
| Asp GAC | Leu TTA | Glu GAA | Ile ATC | 765 Tyr TAT | Pro CCG | Phe TTT | Ile ATT | Thr ACC | 770 Asn AAT | Asn AAT | His CAT | Arg AGA | Glu GAA | 775 Thr ACA | Ile ATC | Glu GAA | Asn AAT | 780 Gly GGT | |
| Thr ACG | Gly GGT | Ser TCC | Leu TTA | 785 Trp TGG | Pro CCG | Ser TCA | Ser TCA | Ala GCC | 790 Gln CAA | Pro CCA | His CAT | Ile ATC | Gly GGA | 795 Lys AAG | Cys TGT | Pro CCA | Pro CCG | 800 Asn AAT | |

TABLE 3-continued

| Pos | AA | Codon | Pos | AA | Codon | Pos | AA | Codon | Pos | AA | Codon | Pos | AA | Codon |
|---|---|---|---|---|---|---|---|---|---|---|---|---|---|---|
| | Arg | CGA | | Cys | TGC | | Ala | GCG | | Pro | CCA | 805 | His | CAC |
| | Leu | CTT | | Glu | GAA | | Trp | TGG | | Asn | AAT | 810 | Pro | CCT |
| | Asp | GAC | | Leu | TTA | | Cys | TGT | 815 | Ser | TCG | | Arg | AGG |
| | Asp | GAT | | Gly | GGA | 820 | Glu | GAA | | | | | | |
| | Lys | AAG | | Cys | TGT | | Ala | GCC | | Pro | CCA | 825 | His | CAT |
| | Ser | TCG | | Phe | TTC | | His | CAT | | Ser | TCC | 830 | Ser | TCC |
| | Phe | TTC | | Asp | GAC | | Ile | ATT | 835 | Val | GTA | | Gly | GGA |
| | Thr | ACA | | Asp | GAC | 840 | Leu | TTA | | | | | | |
| | Asn | AAT | | Glu | GAG | | Asp | GAC | | Leu | CTA | 845 | Gly | GGT |
| | Val | GTA | | Phe | TTT | | Trp | TGG | | Ile | ATC | 850 | Phe | TTT |
| | Lys | AAG | | Leu | TTA | | Lys | AAG | 855 | Gln | CAA | | Gly | GGG |
| | His | CAC | | Ala | GCT | 860 | Arg | AGA | | | | | | |
| | Leu | CTA | | Gly | GGG | | Asn | AAT | | Leu | CTA | 865 | Glu | GAG |
| | Leu | CTC | | Trp | TGG | | Ile | ATT | | Lys | AAG | 870 | Lys | AAA |
| | Pro | CCA | | Val | GTA | | Gly | GGA | 875 | Glu | GAA | | Leu | CTA |
| | Ala | GCT | | His | CAC | 880 | Val | GTG | | | | | | |
| | Lys | AAA | | Arg | AGA | | Ala | GCA | | Pro | CCA | 885 | Lys | AAA |
| | Lys | AAA | | Trp | TGG | | Arg | AGA | | Val | GTA | 890 | Lys | AAA |
| | Val | GTA | | Lys | AAA | | Arg | AGA | | Leu | TTG | 895 | Glu | GAA |
| | Glu | GAA | | Thr | ACA | 900 | Ile | ATC | | | | | | |
| | Val | GTT | | Tyr | TAT | | Ala | GCA | | Asp | GAT | 905 | Ala | GCA |
| | Glu | GAA | | Ile | ATT | | Ala | GCC | | His | CAT | 910 | Asp | GAT |
| | Phe | TTT | | Val | GTA | | Lys | AAA | 915 | Asn | AAC | | Trp | TGG |
| | Val | GTT | | Tyr | TAT | 920 | Gln | CAA | | | | | | |
| | Leu | TTA | | Gln | CAA | | Ala | GCG | | Tyr | TAT | 925 | Thr | ACG |
| | Asn | AAT | | Met | ATG | | Ser | TCT | | Ala | GCA | 930 | Ile | ATT |
| | Phe | TTT | | Ala | GCA | | Ala | GCT | 935 | Lys | AAA | | Cys | TGT |
| | Thr | ACA | | His | CAT | 940 | Ile | ATT | | | | | | |
| | Arg | CGA | | Gly | GGT | | Asp | GAT | | Tyr | TAT | 945 | Leu | CTG |
| | Arg | CGT | | Ser | TCT | | Leu | CTA | | Pro | CCG | 950 | Val | GTG |
| | Ala | GCT | | Ala | GCT | | Tyr | TAT | 955 | Asn | AAT | | Glu | GAA |
| | Thr | ACA | | Val | GTC | 960 | Glu | GAA | | | | | | |
| | Glu | GAA | | Leu | TTA | | Gly | GGT | | Phe | TTC | 965 | Arg | CGT |
| | Gly | GGC | | Thr | ACT | | Leu | CTG | | Ser | TCC | 970 | Phe | TTC |
| | Cys | TGC | | Pro | CCG | | Val | GTG | | Lys | AAA | 975 | Ala | GCG |
| | Asn | AAT | | Val | GTA | 980 | Lys | AAA | | | | | | |
| | Asn | AAT | | Gly | GGT | | Asp | GAT | | Phe | TTT | 985 | Asn | AAT |
| | Arg | CGT | | Gly | GGC | | Leu | TTA | | Asn | AAC | 990 | Cys | TGC |
| | Pro | CCT | | Ala | GCG | | Ala | GCT | | Trp | TGG | 995 | Gly | GGG |
| | Arg | CGT | | Asn | AAT | 1000 | Glu | GAA | | | | | | |
| | Glu | GAA | | Gln | CAA | | Asn | AAC | | Asp | GAT | 1005 | His | CAC |
| | Pro | CCG | | Ser | TCG | | Gly | GGT | | Leu | CTT | 1010 | Val | GTT |
| | Glu | GAG | | Phe | TTC | | Arg | CGT | | Arg | CGT | 1015 | Glu | GAA |
| | Ala | GCG | | Val | GTG | 1020 | Gln | CAA | | | | | | |
| | Glu | GAA | | Val | GTT | | Arg | CGT | | Asn | AAC | 1025 | Cys | TGT |
| | Pro | CCG | | Gly | GGT | | Gly | GGC | | Leu | CTT | 1030 | Tyr | TAT |
| | Leu | CTT | | Gly | GGA | | Arg | CGT | 1035 | Thr | ACA | | Tyr | TAC |
| | Lys | AAG | | Val | GTG | 1040 | Gly | GGA | | | | | | |
| | Tyr | TAT | | Gly | GGA | | Glu | GAA | | His | CAJ | 1045 | Cys | TGC |
| | Glu | GAG | | Val | GTA | | Ile | ATT | | Ile | ATC | 1050 | Glu | GAG |
| | Asn | AAT | | Gly | GGT | | Asn | AAT | | Ile | ATC | 1055 | Thr | ACA |
| | Asp | GAC | | Leu | CTG | 1060 | Phe | TTT | | | | | | |

TABLE 3-continued

| | | | | 1065 | | | | | 1070 | | | | | 1075 | | | | | 1080 |
|---|---|---|---|---|---|---|---|---|---|---|---|---|---|---|---|---|---|---|---|
| Ser AGC | Asn AAC | Cys TGT | Val GTA | Glu GAA | Glu GAG | Glu GAA | Val GTA | Tyr TAT | Pro CCA | Asn AAC | Asn AAC | Thr ACG | Val GTA | Thr ACG | Cys TGT | Asn AAT | Asp GAT | Tyr TAT | Thr ACT |
| | | | | 1085 | | | | | 1090 | | | | | 1095 | | | | | 1100 |
| Ala GCG | Thr ACT | Gln CAA | Glu GAA | Glu GAA | Tyr TAT | Glu GAG | Ala GCT | Thr ACG | Tyr TAC | Thr ACT | Ser TCT | Arg CGT | Asn AAT | Arg CGA | Gly GGA | Tyr TAT | Asp GAC | Gly GGA | Ala GCC |
| | | | | 1105 | | | | | 1110 | | | | | 1115 | | | | | 1120 |
| Tyr TAT | Glu GAA | Ser AGC | Asn AAT | Ser TCT | Ser TCT | Val GTA | Pro CCA | Ala GCT | Asp GAT | Tyr TAT | Ala GCA | Ser TCA | Ala GCC | Tyr TAT | Glu GAA | Glu GAA | Lys AAA | Ala GCA | Tyr TAT |
| | | | | 1125 | | | | | 1130 | | | | | 1135 | | | | | 1140 |
| Thr ACA | Asp GAT | Gly GGA | Arg CGA | Arg AGA | Asp GAC | Pro CCA | Asn AAT | Pro CCT | Glu GAA | Ser TCT | Asn AAC | Asn AAC | Arg AGA | Tyr TAT | Gly GGG | Asp GAT | Tyr TAC | Thr ACA | Pro CCA |
| | | | | 1145 | | | | | 1150 | | | | | 1155 | | | | | 1160 |
| Leu CTA | Pro CCA | Ala GCT | Gly GGC | Tyr TAT | Tyr TAT | Pro CCT | Lys AAA | Cys TGT | Leu TTA | Glu GAG | Tyr TAC | Phe TTC | Pro CCA | Glu GAA | Thr ACC | Asp GAT | Lys AAG | Val GTA | Trp TGG |
| | | | | 1165 | | | | | 1170 | | | | | 1175 | | | | | 1180 |
| Ile ATT | Glu GAG | Ile ATC | Gly GGA | Glu GAA | Thr ACG | Gly GGA | Gly GGA | Thr ACA | Phe TTC | Ile ATC | Glu GAG | Asp GAC | Ser AGC | Val GTG | Glu GAA | Asp GAT | Leu CTT | Leu CTT | Met ATG |
| | | | | 1185 | | | | | 1190 | | | | | 1195 | | | | | 1200 |
| Glu GAG | Glu GAA | Gly GGA | *** TAA | ATG | CTT | TAA | AAT | GTA | TAT | TGT | GCA | AAT | AAA | GAA | TGA | TTA | CTG | ACT | TGT |
| | | | | 1205 | | | | | 1210 | | | | | 1215 | | | | | 1220 |
| ATT | GAC | AGA | TAA | ATA | AGG | AGG | TTA | TTT | TAT | GAA | TAA | AAA | ACG | GGC | TTA | ACT | CTT | AAA | AGA |
| | | | | 1225 | | | | | 1230 | | | | | 1235 | | | | | |
| ATG | ATG | TCC | GTT | TTT | TGT | ATA | ATT | TAA | CGA | GTG | ATA | TAA | AAA | TGT | TTT | TTT | GCG | AAG | G |

We claim:

1. A hybrid gene comprising DNA encoding a B.t. toxin having the amino acid sequence shown in FIG. 1.

2. DNA, according to claim 1, having the nucleotide sequence shown in Table 1.

3. DNA, according to claim 1, having the nucleotide sequence shown in Table 1, wherein said sequence terminates at the stop codon.

4. Essentially pure toxin, active against lepidopteran insects, having the amino acid sequence shown in FIG. 1.

5. A recombinant DNA transfer vector comprising DNA having the nucleotide sequence which codes for the amino acid sequence shown in FIG. 1.

6. The DNA transfer vector, according to claim 5, transferred to and replicated in a prokaryotic or eukaryotic host.

7. A bacterial host transformed to express a B.t. toxin having the amino acid sequence shown in FIG. 1.

8. *Pseudomonas florescens,* according to claim 7, transformed with a plasmid vector containing the B.t. toxin gene encoding with the B.t. toxin having the amino acid sequence shown in FIG. 1.

9. *Pseudomanas fluorescens (M2,16-11),* having the identifying characteristic of NRRL B-18292, a *Pseudomonas fluorescens according to claim 8.*

10. A microorganism according to claim 7, which si a species of Pseudomonas or *Escherichia coli.*

11. A microorganism according to claim 10, wherein said microorganism is pigmented and phylloplane adherent.

12. A method for controlling lepidopteran insects which comprises administering to said insects or to the environment of said insects a microorganism according to claim 10.

13. A method according to claim 12, wherein said administration is to the rhizosphere.

14. A method according to claim 13, wherein said administration is to the phylloplane.

15. A method according to claim 12, wherein said administration is to a body of water.

16. An insecticidal composition comprising insecticide containing substantially intact, treated cells having prolonged pesticidal activity when applied to the environment of a target pest, wherein said insecticide is a polypeptide toxic to lepidopteran insects, is intracellular, and is produced as a result of expression of a transformed microbe capable of expressing the B.t. toxin having the amino acid sequence shown in FIG. 1.

17. The insecticidal composition, according to claim 16, wherein said treated cells are treated by chemical or physical means to prolong the insecticidal activity in the environment.

18. The insecticidal composition, according to claim 17, wherein said cells are prokaryotes.

19. The insecticidal composition, according to claim 18, wherein said prokaryote cells are selected from the group consisting of Enterobacteriacaeae and Pseudomonadaceae.

20. Treated, substantially intact unicellular microorganism cells containing an intracellular toxin, which toxin is a result of expression of a *Bacillus thuringiensis* toxin gene toxic to lepidopteran insects which codes for a polypeptide toxin having the amino acid sequence shown in FIG. 1, wherein said cells are treated under conditions which prolong the insecticidal activity when said cell is applied to the environment of a target insect.

21. The cells, according to claim 22, wherein the cells are treated by chemical or physical means to prolong the insecticidal activity in the environment.

22. The cells according to claim 20, wherein said microorganism is Pseudomonas and said toxin is a B.t. toxin having the amino acid sequence shown in FIG. 1.

23. Pseudomonas cells according to claim 22, wherein said cells are treated with iodine.

24. The cells, according to claim 20, which are *Pseudomonas fluorescens.*

25. The cells, according to claim 24, which are *Pseudomonas fluorescens* (pM2,16-11).

26. A plasmid selected from the group consisting of pKK2, pKK73BB-9, pKK1-73, pl,123-1, pl,130-6 and pM2,16-11.

27. Plasmid pM2,16–11, according to claim 26.

* * * * *

UNITED STATES PATENT AND TRADEMARK OFFICE
CERTIFICATE OF CORRECTION

PATENT NO. : 5,128,130
DATED : July 7, 1992
INVENTOR(S) : Thomas E. Gilroy, et al It is certified that error appears in the above-indentified patent and that said Letters Patent is hereby corrected as shown below:

Column 5, line 2: "Lactobacil laceae" should read --Lactobacillaceae--.

Column 5, lines 37: "a microbe physical means," should read --a microbe containing the *B.t.* toxin gene, can be by chemical or physical means--.

Column 6, line 64: "phosphatose" should read --phosphatase--

Column 27, line 25: "(M2, 16-11)" should read --(pM2, 16-11)--.
Column 27, line 27: "*according to claim 8.*" should read --according to claim 8.--

Signed and Sealed this

Fifth Day of October, 1993

*Attest:*

BRUCE LEHMAN

*Attesting Officer*   *Commissioner of Patents and Trademarks*